(12) United States Patent
Fretel et al.

(10) Patent No.: US 10,114,204 B2
(45) Date of Patent: Oct. 30, 2018

(54) APPARATUS AND METHOD FOR OPTICAL BEAM SCANNING MICROSCOPY

(71) Applicant: HORIBA JOBIN YVON SAS, Longjumeau (FR)

(72) Inventors: Emmanuel Fretel, Croix (FR); Damien Andrezejeusky, Villeneuve d'Ascq (FR); Rene Boidin, Beuvry la Foret (FR); Philippe De Bettignies, Lambersart (FR)

(73) Assignee: HORIBA JOBIN YVON SAS, Longjumeau (FR)

( * ) Notice: Subject to any disclaimer, the term of this patent is extended or adjusted under 35 U.S.C. 154(b) by 0 days.

(21) Appl. No.: 15/304,632

(22) PCT Filed: Apr. 17, 2015

(86) PCT No.: PCT/FR2015/051055
§ 371 (c)(1),
(2) Date: Oct. 17, 2016

(87) PCT Pub. No.: WO2015/159035
PCT Pub. Date: Oct. 22, 2015

(65) Prior Publication Data
US 2017/0045722 A1    Feb. 16, 2017

(30) Foreign Application Priority Data

Apr. 17, 2014   (FR) ..................................... 14 53479

(51) Int. Cl.
*G02B 21/00* (2006.01)
*G01J 3/06* (2006.01)
(Continued)

(52) U.S. Cl.
CPC ............ *G02B 21/0048* (2013.01); *G01J 3/06* (2013.01); *G01J 3/44* (2013.01); *G01N 21/65* (2013.01);
(Continued)

(58) Field of Classification Search
None
See application file for complete search history.

(56) References Cited

U.S. PATENT DOCUMENTS

2005/0128476 A1   6/2005  Zhao
2010/0128342 A1*  5/2010  Abramovitch ....... G01Q 10/065
                                                          359/325

(Continued)

FOREIGN PATENT DOCUMENTS

EP       1 983 332 A1     10/2008
JP       2001 091848 A     4/2001
WO       2010/069987 A1    6/2010

OTHER PUBLICATIONS

International Search Report, dated Jul. 27, 2015, from corresponding PCT application.

*Primary Examiner* — Jennifer D. Carruth
(74) *Attorney, Agent, or Firm* — Young & Thompson

(57) ABSTRACT

An optical beam scanning microscopy apparatus includes a light source adapted to emit an optical beam (2) and a microscope objective (1) adapted for focusing the optical beam (2) in an object plane (11). The microscopy apparatus includes first and second reflecting optical elements (M-X1, M-X2) disposed in series on the optical path of the optical beam (2) between the light source and the microscope objective (1), first elements of angular tilting (21, 25) adapted for tilting the first reflecting optical elements (M-X1, M-XY1) according to a first predetermined rotation angle (RX1), and second elements of angular tilting (22, 26) adapted for tilting the second reflecting optical elements
(Continued)

(M-X2, M-XY2) according to a second rotation angle (RX2), in such a way as to angularly tilt the axis (12) of the optical beam (2) by pivoting about the center (O) of the pupil of the microscope objective (1).

10 Claims, 8 Drawing Sheets

(51) Int. Cl.
 *G01J 3/44* (2006.01)
 *G01N 21/65* (2006.01)
 *G02B 26/10* (2006.01)
(52) U.S. Cl.
 CPC ..... *G02B 21/0032* (2013.01); *G02B 21/0076* (2013.01); *G02B 26/101* (2013.01); *G02B 26/105* (2013.01); *G01N 2021/656* (2013.01)

(56) References Cited

U.S. PATENT DOCUMENTS

| | | |
|---|---|---|
| 2011/0249311 A1 | 10/2011 | Engelhardt |
| 2014/0092459 A1* | 4/2014 | Mizuta ................ G02B 21/002 359/201.2 |

* cited by examiner

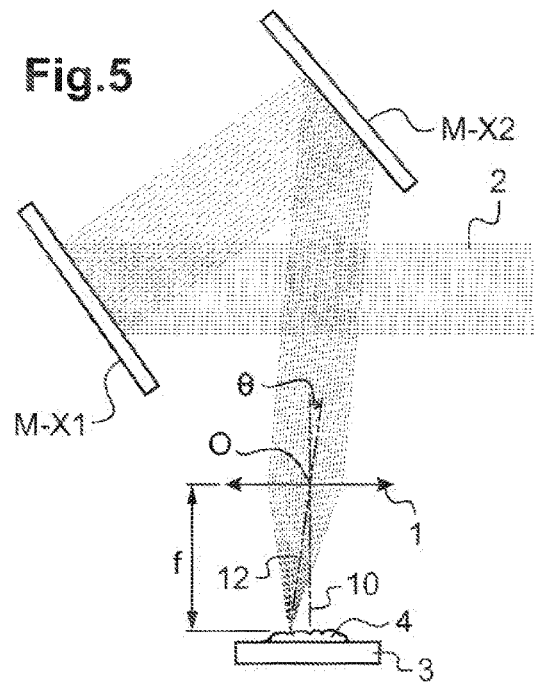
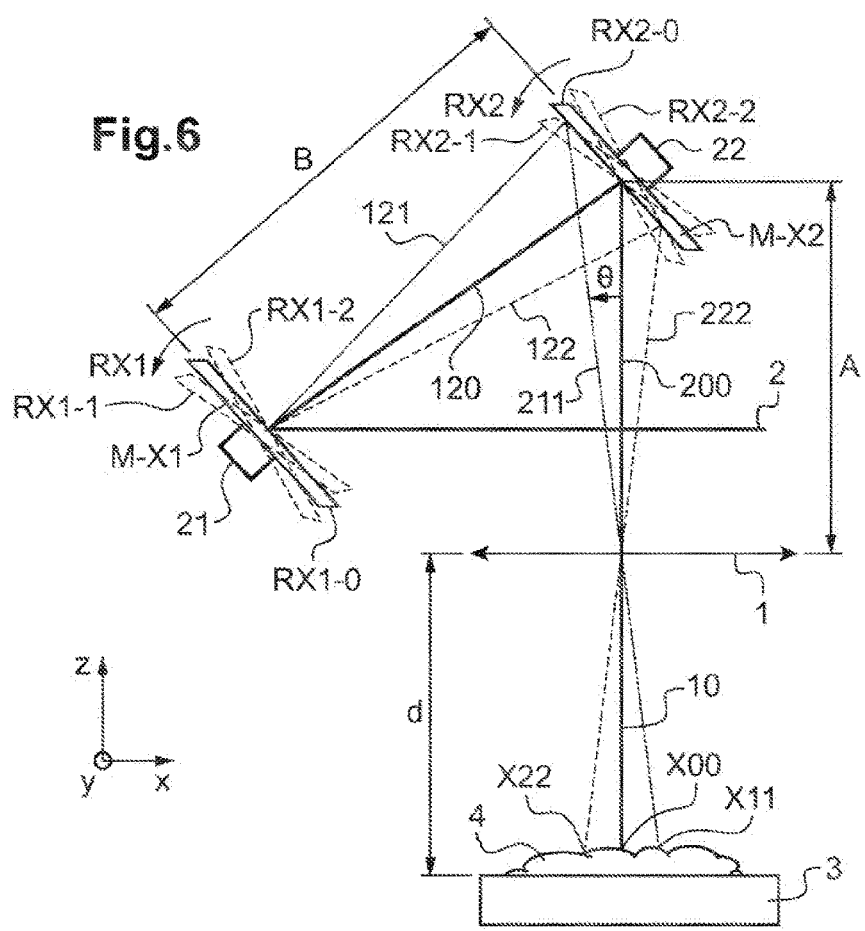

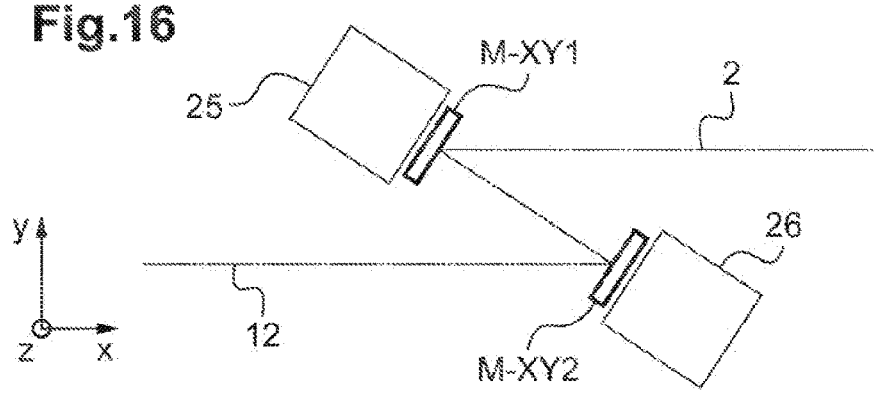
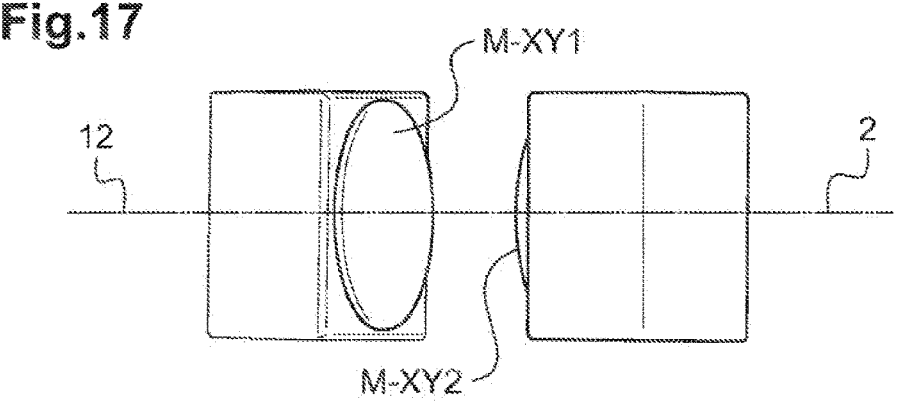
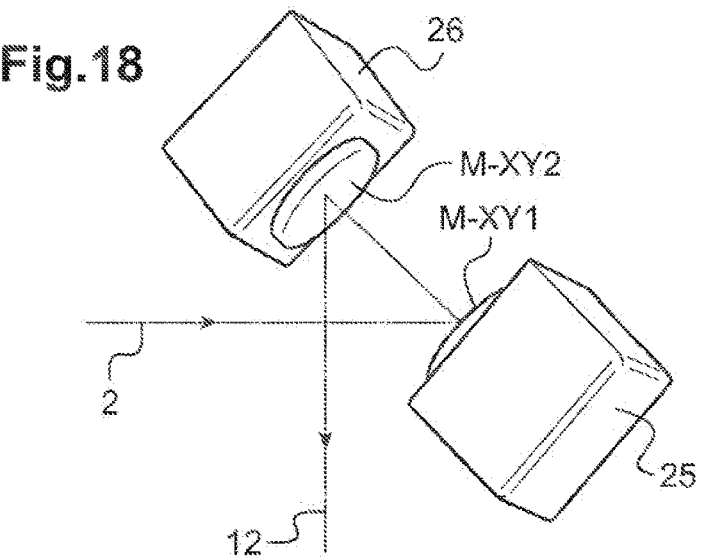

APPARATUS AND METHOD FOR OPTICAL BEAM SCANNING MICROSCOPY

BACKGROUND OF THE INVENTION

Field of the Invention

This invention generally relates to the field of apparatuses and methods for optical beam scanning or optical beam angular displacement microscopy.

It more particularly relates to an apparatus and method for scanning laser beam Raman micro-spectrometry.

Description of the Related Art

The invention also applies to other forms of optical beam scanning optical microscopy such as photoluminescence, fluorescence or cathodoluminescence microscopy. In these apparatuses for scanning optical microscopy, the optical scanning beam can be a laser beam or a beam emitted by a light-emitting diode (LED), as for example in a spectrofluorimeter of the TCSPC (time-correlated single photon counting) type.

It is known in particular in patent document EP1983332A a method of spectroscopic imaging and a sample surface scanning exploration system. Document EP1983332A describes a spectroscopic imaging apparatus comprising a scanning device, also called a scanner, to explore the surface of a fixed sample via angular displacement of an excitation laser beam according to orthogonal directions. More precisely, document EP1983332A describes a scanning device placed in the tube of a confocal microscope in such a way as to be inserted between the microscope objective and the injection-rejection filter of a Raman spectrometer. The scanning device comprises two galvanometric mirrors disposed in series on the optical path of the laser beam. The two galvanometric mirrors have mutually transverse axes of rotation in order to angularly displace the laser beam according to orthogonal directions on the surface of the sample. The optical system with two mirrors operates in one direction to angularly displace the excitation laser beam in such a way as to position it at different points of the surface of the sample. By inverse-return of the light, this optical system with two mirrors operates in the reverse direction in order to collect a Raman back-scattering beam and transmit it in the direction of a detection system, for example a Raman spectrometer. The advantage of this system is that the laser source and the detection system remain fixed. This apparatus makes it possible to acquire an image by Raman spectrometry of a portion of the surface of a sample with a resolution of about 50×50 points in about ten minutes.

Other patent documents describe apparatuses for beam scanning microscopy (see for example WO 2010/069987, US 2005/128476 or JP 2001 091848).

The dimension of the scanned zone on the sample depends in particular on the magnification of the microscope objective used. For the same amplitude of rotation of the mirrors, the change in the magnification of the microscope objective makes it possible to modify the extent of the scanned surface on the sample.

The microscope objectives used can be of different types: standard, with a long working distance (Long Working Distance or LWD), adapted for the visible and/or the ultraviolet range.

However, regardless of the magnification of the microscope objective, it is observed in practice that the extent of the surface that can be accessed by angular displacement of the laser beam on the surface of the sample is clearly less than the optical field of the microscope objective. In this document, object field means the optical field in the focal plane of the microscope objective.

Thus, by way of example, different microscope objectives are used such as magnification objectives 100×, 50× and 10×. Each microscope objective is defined by a numerical aperture (or NA), a focal distance, a field number (or FN) and a diameter.

A maximum width of the optical field is calculated according to the frontal distance which corresponds to the distance between the front face of the objective and the sample.

In practice, the maximum width of the optical field of a microscope objective is calculated by applying the following formula:

Width of the field=Field number/Magnification.

The following table indicates the values of the parameters of different objectives of the OLYMPUS brand of the Mplan N 100×, 50× and 10× type respectively:

TABLE 1 optical properties of different microscope objectives

| | Olympus MPLAN N 100X | Olympus MPLAN N 50X | Olympus MPLAN N 10X |
|---|---|---|---|
| Numerical Aperture | 0.90 | 0.75 | 0.25 |
| Focal distance | 1.8 mm | 3.6 mm | 18 mm |
| Field Number | 22 mm | 22 mm | 22 mm |
| Diameter of the lens | 3.24 mm | 5.4 mm | 9 mm |
| Maximum width of the optical field | 220 μm | 440 μm | 2200 μm |

The maximum width of the optical field indicated in the table hereinabove corresponds to the length of the optical field for imaging through the microscope objective.

However, in practice, the field width that can be accessed by scanning or angular displacement of a laser beam through each one of these microscope objectives is in practice clearly less than the maximum width of the field of the objective considered.

Thus, for an Olympus MPLAN N 50× objective, it is experimentally measured that the width of the field of the two-axis laser scanning microscopy apparatus, called a DuoScan, that is effectively accessible is about +−27 microns, while the maximum width of the optical field of this objective is 440 microns. Likewise, for an Olympus MPLAN N 10× objective, the laser scanning field of the Duoscan is about 200 microns, while the maximum width of the optical field of this objective is 2200 microns.

This limitation in the width of the field that can be accessed by laser scanning is due to the vignetting of the laser beam on the apertures of the optical components. In order to limit this effect, there is a need to reduce the diameter of the laser beam, which has for harmful effect to reduce the spatial resolution (lambda/NA) because the effective numerical aperture of the microscope objective is reduced by sub-covering the pupil.

In order to extend the spatial exploration zone of a laser scanning beam on a sample, various solutions have been proposed. A first solution consists in changing the microscope objective in order to reduce the magnification. A disadvantage of changing the magnification is that the spatial resolution of the measurements is proportional to the magnification of the objective. Another solution consists in combining a scanning by angular tilting of the axis of the laser beam with a relative displacement of the sample with respect to the microscope objective.

However, changing a microscope objective or the displacement of sample holder takes time. In addition, these operations induce a discontinuous modification of the field imaged by the microscopy apparatus. A series of contiguous images is generally obtained which are difficult to recombine in order to form a complete image of the sample on an extended zone with good spatial resolution.

Another limitation is the quality of the measurements of Raman spectrometry obtained by scanning. It is in effect observed that the quality of the measurements of scanning Raman microspectrometry is less than the quality of the measurements taken without scanning, for measurement acquisition parameters that are moreover identical.

In addition, it is not possible to directly view on the image of a camera, the position of the scanning beam on the sample. It is therefore difficult to control the location of the laser beam, for example in applications for measuring biochips.

BRIEF SUMMARY OF THE INVENTION

One of the purposes of the invention is to increase the width of the field that can be accessed by optical beam scanning in a scanning microscopy apparatus in order to approach the maximum width of the optical field of this microscopy apparatus.

One of the purposes of the invention is to increase the spatial extend of the measuring field without modifying the spatial resolution of the measurements or the quality of the measurements.

Another purpose of the invention is to improve the quality of the measurements of scanning Raman microspectrometry while still decreasing the acquisition time for the measurements.

Another purpose of the invention is to limit intensity losses on an incident laser beam and on a Raman scattering beam.

In order to overcome the aforementioned disadvantages of prior art, this invention proposes an apparatus for optical beam scanning microscopy comprising at least one light source adapted to emit an optical beam, a microscope objective having an entrance pupil, the microscope objective being arranged according to a longitudinal optical axis of the microscopy apparatus, with the pupil having a center on the longitudinal optical axis, and the microscope objective being adapted for focusing said optical beam in an object plane transverse to the longitudinal optical axis and means for the angular displacement of the optical beam according to at least one spatial direction (X, Y) in the object plane.

More particularly, according to the invention an apparatus for optical beam scanning microscopy is proposed wherein said means for the angular displacement of the optical beam comprise:

first reflecting optical means and second reflecting optical means disposed in series on the optical path of the laser beam between the laser source and the microscope objective, first means of angular tilting adapted for tilting said first reflecting optical means according to a first predetermined rotation angle, and second means of angular tilting adapted for tilting said second reflecting optical means according to a second predetermined rotation angle as a function of said first rotation angle, in such a way as to angularly tilt the axis of the optical beam by pivoting about the center of the pupil of the microscope objective, said optical beam remaining centered on the center of the pupil of the microscope objective in a range of tilting angles of the axis of the optical beam with respect to the longitudinal optical axis, in such a way as to displace the optical beam according to said at least one direction in the object plane.

The invention advantageously makes it possible to increase the amplitude of the displacement of the optical beam in the focal plane of the microscope objective in an apparatus for optical beam scanning microscopy.

In a particular embodiment, said means for the angular displacement of the optical beam further comprise:

third reflecting optical means and fourth reflecting optical means disposed in series on the optical path of the laser beam between the laser source and the microscope objective, third means of angular tilting adapted to tilt said third reflecting optical means according to a third predetermined rotation angle, and fourth means of angular tilting adapted to tilt said fourth reflecting optical means according to a fourth predetermined rotation angle as a function of said third rotation angle in such a way as to angularly tilt the axis of the optical beam by pivoting about the center of the pupil of the microscope objective, said optical beam remaining centered on the center of the pupil of the microscope objective in a range of tilting angles of the axis of the optical beam with respect to the longitudinal optical axis in such a way as to displace the optical beam according to another direction in the object plane.

Other non-limiting and advantageous characteristics of an apparatus for optical beam scanning microscopy in accordance with the invention are as follows:

the first reflecting optical means and the third reflecting optical means are formed by a same first mirror;

the second reflecting optical means and the fourth reflecting optical means are formed by a same second mirror;

the first mirror is mounted on an actuator with two axes of rotation, for example of the piezoelectric type or a voice coil, and/or the second flat mirror is mounted on an actuator with two axes of rotation, for example of the piezoelectric or voice coil type;

the first reflecting optical means are formed from a first mirror and the second reflecting optical means are formed from a second mirror;

the third reflecting optical means are formed from a third mirror and the fourth reflecting optical means are formed from a fourth mirror;

the first mirror is mounted on an actuator with one axis of rotation, for example of the galvanometric type, the second mirror is mounted on an actuator with one axis of rotation, the third mirror is mounted on an actuator with one axis of rotation and/or the fourth mirror is mounted on an actuator with one axis of rotation;

the actuator of the first mirror comprises a position sensor that supplies a position signal and the actuator of the second mirror comprises a position sensor, with the apparatus comprising a phase locked loop system adapted to drive a control signal of the actuator of the second mirror as a function of the position signal of the actuator of the first mirror and/or the actuator of the third mirror comprises another position sensor that supplies another position signal and the actuator of the fourth mirror comprises another position sensor, with the apparatus comprising a phase locked loop system adapted to drive a control signal of the actuator of the fourth mirror as a function of the position signal of the actuator of the third mirror;

the second rotation angle is function of the first rotation angle, the distance B between the first reflecting optical means and the second reflecting optical means, the distance A between the second reflecting optical means and the center of the entrance pupil of the microscope objective;

the microscopy apparatus comprises a plurality of microscope objectives having different magnifications;

said at least one light source comprises one or several sources of the laser source and/or light-emitting diode type.

In particular embodiments of an apparatus for optical beam scanning microscopy in accordance with the invention, the apparatus further comprises:

a beam expander disposed between said at least one light source and the microscope objective, with the beam expander having a fixed and/or variable magnification;

a viewing camera adapted to form an image of the object plane of the microscope objective and/or for viewing a zone of a sample scanned with optical beam scanning;

a white light source adapted to illuminate a sample in the object plane;

a confocal hole disposed in a plane optically conjugated with the object plane and means for collimating the optical beam disposed between the at least one light source and the microscope objective in order to form a collimated optical beam, the first reflecting optical means and the second reflecting optical means being disposed in series on the optical path of the collimated optical beam.

In a particular and advantageous embodiment, the apparatus for optical beam scanning microscopy is combined with a Raman spectrometer, a coherent anti-Stokes Raman spectrometer (CARS), a fluorescence spectrometer, a photoluminescence spectrometer, or a cathodoluminescence spectrometer adapted to measure and analyze a signal by reflection, transmission and/or scattering of the laser beam on the sample during the angular displacement of the laser beam.

The invention also proposes a method for optical beam scanning microscopy comprising the following steps:

emitting an optical beam by means of at least one light source;

optical reflecting of said optical beam on first reflecting optical means then on second reflecting optical means disposed in series on the optical path of the optical beam between said at least one light source and a microscope objective, tilting of said first reflecting optical means according to a first predetermined rotation angle, tilting of said second reflecting optical means according to a second predetermined rotation angle as a function of the first rotation angle, in such a way as to angularly tilt the axis of the optical beam by pivoting about the center of the pupil of the microscope objective, in a range of tilting angles of the axis of the optical beam with respect to a longitudinal optical axis; and focusing said optical beam in an object plane by means of said microscope objective, in such a way as to displace said optical beam according to at least one spatial direction in the object plane.

Thus, the method of the invention makes it possible to control the position of the optical scanning beam on the center of the pupil of the microscope objective, regardless of the tilting of the optical beam with respect to the optical axis of the microscope objective.

In a particular embodiment, the method for optical beam scanning microscopy further comprises the following steps:

optical reflecting of said optical beam on third reflecting optical means then on fourth reflecting optical means disposed in series on the optical path of the optical beam between said at least one light source and said microscope objective;

tilting of said third reflecting optical means according to a third predetermined rotation angle, tilting of said fourth reflecting optical means according to a fourth predetermined rotation angle as a function of the third rotation angle, in such a way as to angularly tilt the axis of the optical beam by pivoting about the center of the pupil of the microscope objective, in a range of tilting angles of the axis of the optical beam with respect to a longitudinal optical axis; and focusing said optical beam in the object plane by means of said microscope objective, in such a way as to displace said optical beam according to at least one other spatial direction in the object plane.

The invention will have a particularly advantageous application in imaging via laser beam angular displacement microscopy, in such a way as to scan the surface of a sample in order to form an image of the sample, for example Raman microspectrometry, photoluminescence, Raman microspectrometry of the CARS (Coherent anti-Stokes Raman scattering) type, micro-CARS, Raman probe or two photons microspectrometry.

The invention will also have a particularly advantageous application in microscopy, where the displacement of an optical beam, for example of a laser beam is carried out by discrete steps in order to point the laser beam at predetermined points of a surface, for example in applications for analyzing biochips. A discontinuous laser beam scanning, in steps, makes it possible to probe samples, for example biological samples (bio-chips), every 100 microns on the same surface, then to take a measurement and a one-off analysis (e.g. Raman spectrometry) or via local scanning of a micro-sample. In these applications, the invention makes it possible, without displacement of the bio-chip to explore a larger field and thus to probe a larger number of measured micro-samples, with greater precision in the displacement steps of the laser beam.

The invention shall also have applications in microscopy with continuous scanning of the optical beam.

In a particular and advantageous embodiment, the continuous scanning of an optical beam is synchronized with a detector of the CCD type for example, in order to quickly transfer the record of a scanning line to an electronic memory, in such a way as to quickly form an image of the surface of a scanned sample.

In another embodiment, called a macrospot, the continuous scanning of an optical beam is combined with an integration of the signal detected on a detector, for example of the photomultiplier (PMT) type, in such a way as to average the measurement over a predetermined zone of the sample to be analyzed, and possibly analyze more precisely a zone of the sample where a particular signal is detected.

The system and the method for optical beam scanning microscopy of the invention are compatible with all forms of scanning on the sample according to lines, a square, a circle, etc.

This invention also relates to the characteristics that shall appear in the following description and which must be considered independently or according to any technical permissible combinations thereof.

BRIEF DESCRIPTION OF THE DRAWINGS

This description given by way of a non-limiting example will provide a better understanding of how the invention can be carried out in reference to the annexed drawings wherein:

FIG. 5 diagrammatically shows the scanning of a laser beam on the objective of an apparatus for scanning microscopy according to the invention;

FIG. 6 shows a laser beam scanning system according to a first embodiment of the invention;

FIGS. 16-18 show a laser beam scanning system according to two scanning axes according to a third embodiment of the invention;

DETAILED DESCRIPTION OF THE PREFERRED EMBODIMENTS

Figure 1:
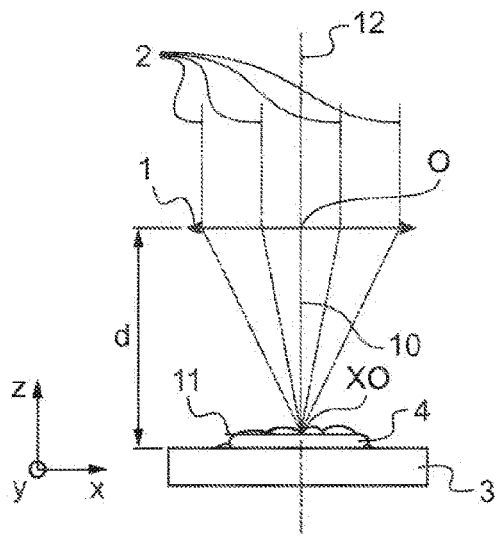
FIGS. 1-2 diagrammatically show the principle of the scanning of a laser beam in order to displace the position of a laser beam on a sample or to scan a sample according to prior art.
Figure 2:
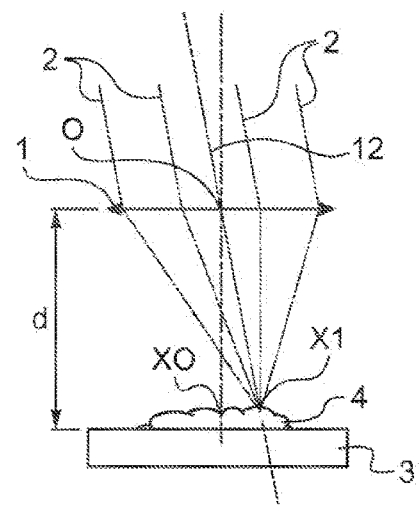

FIGS. 1-2 diagrammatically show the principle of the scanning of a laser beam in order to displace the position of a laser beam on a sample or to scan a sample.

A microscope objective 1 is disposed on the optical axis 10 of a microscopy apparatus. A sample 4 is placed on a sample holder 3 at a distance d from the microscope objective 1. A laser source emits a collimated laser beam 2. A flat mirror (not shown) reflects the laser beam in the direction of the microscope objective 1. The microscope objective 1 focuses the laser beam in the focal plane 11 of the microscope objective 1.

By convention in this document, the optical axis 10 of the microscope objective 1 is parallel to the axis Z in an orthonormed system XYZ and the focal plane 11 of the microscope objective 1 is in an XY plane.

The axis of the laser beam is defined as being the longitudinal optical axis of propagation of the beam. For a laser beam of Gaussian spatial distribution, the axis 12 of the laser beam is located at the center of the laser beam.

In FIG. 1, the axis 12 of the laser beam 2 is parallel and centered on the axis 10 of the microscope objective 1. The laser beam is focused on the focal point X0 of the microscope objective.

In FIG. 2, the axis 12 of the laser beam 2 is angularly tilted, for example by means of a flat mirror arranged on the path of the laser beam 2, with this mirror being mobile in rotation, in such a way that the laser beam is focused in a second point X1 of the focal plane 11. During the scanning of the laser beam, the laser source (not shown) and the microscope objective are in general fixed, with only the mirror being mobile in rotation. The axis of rotation of the mirror is for example parallel to the Y axis and in general close to the reflective surface of the mirror. A rotation of the mirror results in an angular displacement of the laser beam 2. This angular displacement of the laser beam 2 in relation to the optical axis 10 of the microscope objective 1 thus makes it possible to scan the surface of the sample 4 between the points X0 and X1, in a continuous or step-by-step manner. However, this angular displacement due to the rotation of the mirror, produces a decentering of the axis 12 of the laser beam in relation to the center O of the pupil of the microscope objective 1.

For a tilting angle of the laser beam 2 greater than a first threshold value, a phenomenon of vignetting is observed, with a portion of the laser beam being shut off by the edges of the pupil of the microscope objective. The vignetting phenomenon increases with the tilting angle of the laser beam, until a complete shutting off of the laser beam for a second threshold value of the tilting angle. The partial and complete shutting off thresholds of the laser beam depend on the aperture of the pupil of the objective and of the extent of the laser beam. A partial shutting off of the beam is observed which progressively reduces the intensity of the excitation laser beam and, by inverse-return of the light, the intensity of the Raman beam detected. It is therefore observed that the vignetting phenomena limit the zone accessible by angular displacement of the beam on the sample.

In order to limit vignetting in a scanning system with one axis, one possibility is to reduce the diameter of the excitation laser beam. However, a decrease in the diameter of the laser beam produces an increase in the diameter of the beam at the focal point, which results in a decrease in the spatial resolution of the beam scanning microscopy apparatus.

In a system with one scanning axis, such as shown in FIGS. 1-2, the vignetting effects can be reduced by bringing the mirror mobile in rotation closer to the microscope objective 1.

However, beam scanning microscopy apparatuses are in general not limited to a single scanning axis.

Thus, most beam scanning microscopy apparatuses combine the tilting of the beam around two axes of orthogonal rotation in order to angularly displace the beam over the surface of a sample according to two transverse directions.

Figure 3:
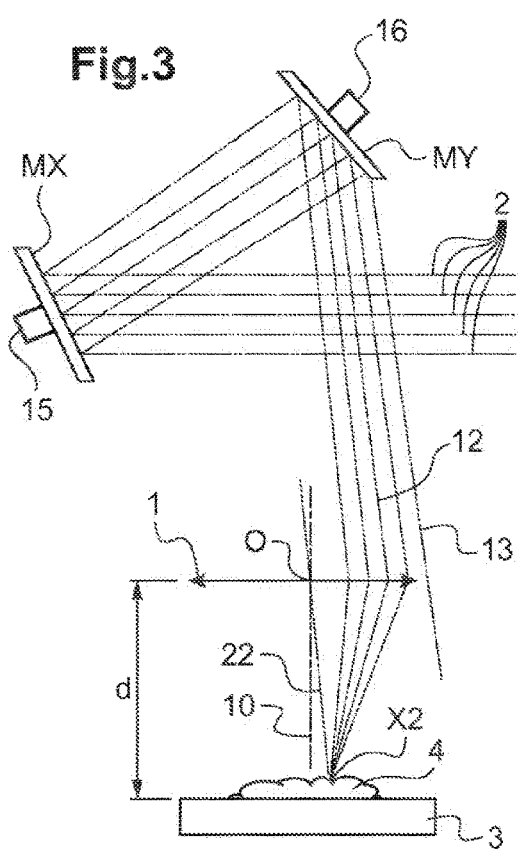
FIGS. 3 and 4 show vignetting phenomena of the laser scanning beam in an apparatus for laser beam scanning microscopy with two scanning axes according to prior art.
Figure 4:
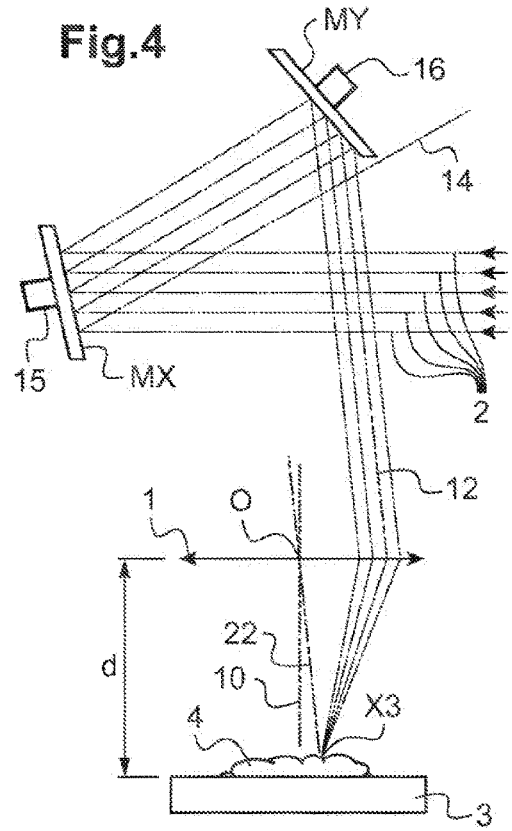

FIGS. 3-4 diagrammatically show as a side view a microscopy apparatus comprising a scanning system with two axes in order to illustrate the principle and analyze the limits of beam scanning with two axes. The same reference signs designate the same elements as in FIGS. 1-2. The scanning system comprises a first flat mirror M-X and a second flat mirror M-Y disposed in series on the optical path of the laser beam 2. The first mirror M-X, provided for example with a galvanometric motor 15, is mobile in rotation about a first axis, for example parallel to the Y axis, in such a way as to induce an angular displacement of the laser beam 2 according to the X axis in the focal plane 11. The second mirror M-Y, provided with a galvanometric motor 16, is mobile in rotation about a second axis, for example parallel to the X axis, in such a way as to induce an angular displacement of the laser beam 2 according to the Y axis in the focal plane 11. The motors 15 and 16 are controlled in order to carry out predetermined rotations and to carry out a path with a defined shape on the surface of the sample.

In Raman microscopy, the laser scanning beam is also the excitation beam which induces the Raman emission by the sample. In back-scattering configuration, the Raman scattering beam is collected in the direction of the incident excitation beam, with this emission-reception direction being fixed. The Raman beam is in general separated from the Raman scattering beam by means of rejection filters, of the notch filter, edge filter or Volume Bragg Grating (or VBG) type. It is known that the very low intensity of the Raman signals in relation to the Rayleigh scattering requires an excellent signal-to-noise ratio. It is therefore essential to illuminate the sample with a beam with sufficient lighting intensity and to collect the greatest portion of the Raman scattering beam.

However, the signal-to-noise ratio in Raman scanning microspectrometry seems limited which results in increasing the acquisition time in order to obtain a complete image. In addition, the object field on the sample is also limited to a field that is much more reduced than the nominal field of the microscope objective.

In the framework of this invention, the limits in signal-to-noise ratio and in scanning field are analyzed as follows.

As shown in FIGS. 3-4, the first mirror M-X and the second mirror M-Y are disposed in series on the optical path of a laser beam 2, between a laser source (not shown) and a microscope objective 1. The axis of the microscope objective is here confounded with the optical axis 10 of the microscope. It is supposed that at rest, i.e. with zero tilting angles, the first and second mirrors M-X, M-Y are arranged in such a way that the axis 12 of the laser beam is confounded with the optical axis 10 of the microscope objective 1, i.e. the optical axis of the laser beam is centered and parallel to the optical axis 10 of the microscope objective 1.

It is sought to displace the laser beam on the sample from a point X0, located at the intersection of the optical axis 10 and of the focal plane 11 of the microscope objective 1, to a point X2, along the X axis. In order to displace the laser beam 2, the galvanometric motor 15 is controlled so that it induces an angular tilting DELTA-X of the first mirror M-X about the Y axis. The incident beam coming from the source remains immobile. The beam reflected on the surface of the mirror M-X is subjected to a rotation by an angle equal to 2×DELTA-X about the Y axis. The beam reflected by the first mirror M-X is displaced thus on the surface of the second mirror M-Y. The second mirror M-Y again reflects the laser beam in the direction of the microscope objective. The beam reflected by the second mirror M-Y is displaced angularly and laterally on the pupil of the microscope objective 1. The axis of the incident laser beam on the microscope objective is tilted by an angle equal to 2×DELTA-X in relation to the optical axis 10 of the microscope objective 1. The microscope objective 1 thus focuses the laser beam at the point X2, located at the intersection of the focal plane of the microscope objective 1 and of a straight line 22 passing by the center O of the pupil of the objective and parallel to the axis 12 of the incident collimated laser beam on the objective.

Similarly, a rotation of the second mirror M-Y by a rotation angle RY about an axis parallel to the X axis produces an angular displacement of the laser beam equal to 2×DELTA-Y. Thus, the rotation of the second mirror M-Y produces an angular displacement of the laser beam on the pupil of the objective 1 and a displacement of the beam focused in the direction Y.

However, for a tilting angle DELTA-X greater than a threshold value, it is observed in FIG. 3 that a ray 13 of the laser beam, located outside the pupil of the objective, is not focused at point X2. Therefore, the intensity of the incident laser beam on the sample is reduced. The vignetting phenomenon can explain a drop in the signal-to-noise ratio for the points measured on the edges of the field, which correspond to tilting angles greater than a certain threshold value. For a tilting angle of the first mirror M-X greater than another threshold value, the laser beam is entirely shut off by the pupil of the microscope objective.

Analog limitations come from the tilting by an angle DELTA-Y of the laser beam by the second mirror M-Y on the microscope objective 1.

Similar to the single-axis scanning system, the scanning system with two axes can therefore be limited by vignetting phenomena due to the angular displacements of the first axis and/or of the second axis on the pupil of the microscope objective.

On the other hand, FIG. 4 shows another vignetting effect of the laser beam in a system with two scanning axes. FIG. 4 shows the laser beam inclined by an angle DELTA-X by means of the first mirror M-X and of the first galvanometric motor 15. The displacement of the laser beam on the surface of the second mirror M-Y is such that a ray 14 of the laser beam is located outside the pupil of the second mirror M-Y. The second mirror M-Y therefore cannot reflect the ray 14 in the direction of the microscope objective. This ray 14 is therefore not focused on the point X3 on the sample. By extrapolating the tilting of the laser beam of FIG. 4, it is observed that the laser beam is entirely shut off by the pupil of the second mirror M-Y when tilting angle DELTA-X is greater than a second threshold value of the tilting angle.

According to the dimension of the second mirror M-Y, a scanning system with two axes can therefore also be limited by vignetting phenomena due to the angular displacement of the beam in relation to the pupil of the second mirror M-Y.

Similarly, the angular tilting of the first mirror M-X in relation to the excitation laser beam can produce vignetting phenomena, when the diameter of the laser beam is greater than the apparent diameter of the pupil of the first mirror M-X.

The results of this analysis are that, in a scanning microscopy apparatus according to two axes, the displacements of the laser beam in the focal plane along the X axis and/or respectively the Y axis, are thus limited by vignetting effects due to the pupil of the first mirror M-X, of the second mirror M-Y and/or the pupil of the microscope objective.

More generally, the displacement of a laser beam by scanning in a microscopy apparatus is limited in transverse field and in intensity by vignetting phenomena due to the optical system formed of the different optical components disposed in series on the optical path of the laser beam. These vignetting phenomena seem in particular due to the scanning mirrors M-X, M-Y and/or to the microscope objective 1.

However, in a system with two scanning axes, the encumbrance of the two reflector mirrors M-X, M-Y disposed in series on the optical path of the laser beam, do not make it possible to effectively reduce the distance between the first mirror and the microscope objective, to the extent that the vignetting effects remain substantial.

It stems from this analysis that the main problem, during the use of a Raman microscopy apparatus with two beam scanning axes, is with the pupil at the entrance of the microscope objective 1, as shown in relation with FIGS. 3 and 4. A portion 13 of the beam arriving on the pupil of the microscope objective does not pass through the aperture of the objective because this portion 13 of the beam is displaced beyond the physical limit of the pupil (FIG. 3). A portion of the excitation laser beam is thus lost. In a configuration for measuring Raman back-scattering, via application of the inverse-return of light, a portion of the back-scattered beam is also shut off by the pupil of the microscope objective. The reduction in intensity of the excitation laser beam and of the Raman scattering beam induces a reduction in the intensity of the Raman scattering signal detected. Moreover, another portion 14 of the beam reflected by the first mirror M-X is deviated outside the pupil of the second mirror and is not reflected the direction of the microscope objective. Likewise, a portion of the Raman back-scattering beam is shut off by the edges of the second mirror M-Y. This other portion of the excitation laser beam 14 and of the corresponding back-scattered beam also induces a reduction in the Raman scattering signal detected. Moreover, the beams 13 and 14 which are not reflected in the direction of the sample, can be reflected on other surfaces and thus be the source of parasite beams which also contribute to reducing the signal-to-noise ratio of the Raman scattering signal detected.

The principle of the solution proposed in the framework of this invention shall now be described in relation with FIG. 5. In this figure, the angular tilting of the laser beam is carried out by pivoting the axis of the laser beam around the center O of the entrance pupil of the microscope objective 1. Thus, the laser beam remains centered on the pupil of the microscope objective during the scanning of the beam. This angular tilting makes it possible to reduce the vignetting phenomena in order to limit the losses of intensity on the incident laser beam and in order to increase the field zone that can be accessed by beam scanning.

This displacement is obtained by implementing two mirrors for each scanning axis, with the two mirrors being disposed in series on the optical path of the optical beam 2. For example, the first mirror M-X1 is angularly tilted in such a way as to induce a scanning following the X axis in the focal plane and the second mirror M-X2 is angularly tilted following the same scanning axis X in such a way as to recenter the beam on the pupil of the microscope objective 1.

The displacement X of the beam in the focal plane on the sample for a tilting angle θ of the axis 12 of the beam in relation to the optical axis 10 of the microscope objective is calculated by the following formula:

$$X = f \tan(\theta) \quad (I)$$

In the following table, the displacement X of the beam is deduced therefrom as a function of the tilting angle for different microscope objectives:

TABLE 2 displacement as a function of the tilting angle of the beam on the objective

| Θ (degrees) | 100X | 50X | 10X |
|---|---|---|---|
| 1 | 31 μm | 62 μm | 314 μm |
| 1.5 | 47 μm | 94 μm | 471 μm |
| 2 | 63 μm | 125 μm | 628 μm |
| 2.5 | 78 μm | 157 μm | 785 μm |
| 3 | 94 μm | 189 μm | 943 μm |

The tableau 1 indicates, for an objective 10×, a maximum optical field width of 2.2 mm which corresponds to a field half-width or to a lateral displacement of beam X of 1.1 mm. In table 2, it is observed that a tilting angle θ of 3 degrees of the axis of the beam centered on the axis of this objective 10× makes it possible to cover a field width of 2×943 microns i.e. about 1886 microns, i.e. to practically reach the limit of the optical field width. However a tilting angle of a beam axis of 3 degrees can be obtained by reflection on a mirror and rotation of this mirror by an angle of 1.5 degrees.

FIGS. 6 to 18 show different embodiments that make it possible to obtain a scanning beam following one or two axes by pivoting of the laser beam around the center O of the entrance pupil of the microscope objective, while still maintaining the centering of the laser beam on the center O of the entrance pupil of the microscope objective.

FIG. 6 shows a system with one scanning laser beam axis according to a first embodiment of the invention. The scanning system comprises a first flat mirror M-X1 and a second flat mirror M-X2. The first mirror M-X1 and second mirror M-X2 are disposed in series on the optical path of the laser beam 2 between the laser beam source and the microscope objective 1, for example in the confocal tube of a confocal microscope. The first mirror M-X1 is mobile in rotation about an axis, for example parallel to the Y axis. The second mirror M-X2 is mobile in rotation about an axis which is more preferably parallel to the axis of rotation of the first mirror M-X1 and therefore parallel to the Y axis. Advantageously, a first motor 21 controls the rotation of the first mirror M-X1 and a second motor 22 controls the rotation of the second mirror M-X2. The motors 21, 22 are for example galvanometric motors or step-by-step motors. Preferentially, a control system (not shown) drives the combined angular displacements of the first mirror M-X1 and of the second mirror M-X2.

In an illustrative and in no way limiting manner, FIG. 6 shows different tilting angles of the first mirror M-X1 and of the second mirror M-X2.

In a first orientation of the mirrors of the scanning system, the first mirror M-X1 has a tilting angle RX1-0 and the second mirror M-X2 a tilting angle RX2-0. In this first orientation of the mirrors, the incident laser beam 2 is reflected on the first mirror M-X1 in the direction 120 then on the second mirror M-X2 in the direction 200. The tilting angles RX1-0 of the first mirror M-X1 and RX2-0 of the second mirror are such that the laser beam in the direction 200 is aligned on the optical axis 10 of the microscope objective 1 and centered on the center O of the entrance pupil of the microscope objective 1. In this first configuration, the microscope objective focuses the laser beam at the focal point X0-0. Via inverse-return, the beam back-scattered by the point X00 propagates along the axis 200, is reflected by the second mirror M-X2 then by the first mirror M-X1 in the direction of the incident laser beam 2.

In a second orientation of the mirrors shown in FIG. 6, the first mirror M-X1 has a tilting angle RX1-1 and the second mirror M-X2 a tilting angle RX2-1. In this second orientation of the mirrors, the incident laser beam of axis 12 is reflected on the first mirror M-X1 in the direction 121 then on the second mirror M-X2 in the direction 211. The tilting angles RX1-1 of the first mirror M-X1 and RX2-1 of the second mirror are such that the laser beam in the direction 211 is tilted with respect to the optical axis of the microscope objective 1 while still remaining centered on the center O of the entrance pupil of the microscope objective 1. Advantageously, the first mirror M-X1 produces a tilting of the axis of the beam and the second mirror M-X2 recenters the tilted axis of the beam 211 on the center of the pupil of the objective. In this second configuration, the microscope objective 1 focuses the laser beam at the point X11. An angular displacement of the axis of the beam is thus obtained, from the point X00 to the point X11 on the sample. Via inverse-return, the beam back-scattered by the point X11 propagating in the direction 211 is successively reflected by the mirror M-X2 in the direction 121, then by the mirror M-X1 in the direction of the incident beam 2.

Similarly, in a third orientation of the mirrors shown in FIG. 6, the first mirror M-X1 has a rotation angle RX1-2 and the second mirror M-X2 a rotation angle RX2-2. In this third orientation of the mirrors, the incident laser beam 2 is reflected on the first mirror M-X1 in the direction 122 then on the second mirror M-X2 in the direction 222. The tilting angles RX1-2 of the first mirror M-X1 and RX2-2 of the second mirror are such that the laser beam in the direction 222 is tilted with respect to the optical axis of the microscope objective 1 while still remaining centered on the center O of the entrance pupil of the microscope objective 1. Thus, the first mirror M-X1 produces a tilting of the axis of the beam and the second mirror M-X2 recenters the tilted axis of the beam 222 on the center of the pupil of the objective. In this third configuration, the microscope objective 1 focuses the laser beam at the point X22. An angular displacement of the axis of the beam to the point X22 on the sample is thus obtained. Via inverse-return, the beam backscattered by the point X22 propagating in the direction 222 is successively reflected by the mirror M-X2 in the direction 122, then by the mirror M-X1 in the direction of the incident beam 2.

The combination of a rotation angle of the first mirror M-X1 and of a rotation angle of the second mirror M-X2 therefore makes it possible to obtain an angular offset of the beam which remains centered on the center O of the pupil of the microscope objective.

The tilting angle θ of the axis 211 of the beam in relation to the optical axis 10 is equal to double the rotation angle RX2 of the second mirror M-X2.

In order to calculate the rotation angle of the mirror M-X2 as a function of the tilting of the mirror M-X1, the following equation is used:

$$RX2 = ((ArcSIN(-B \times SIN(2 \times RX1)/A) - 2 \times RX1 + \pi/2)/2 - \pi/4 \quad \text{(II)}$$

Where: RX1 represents the rotation angle of the mirror M-X1 (in radians),
RX2 represents the rotation angle of the mirror M-X2 (in radians);
A the distance of convergence of the rays (in mm), or focal of the objective 1; and
B the distance between the mirrors M-X1 and M-X2 (in mm).

In the particular case where the angles RX1, RX2 are small (in practice less than a few degrees), it is shown that there is a linear relationship between the movement of the two mirrors. In this case, the electronic control system of the rotation of the mirrors is also a linear system and therefore simple.

Finally, in the particular case where B is equal to A, the ratio of the rotation angles between the mirror M-X1 and the mirror M-X2 is equal to 2, and this regardless of the tilting angle θ.

An electronic system can be configured to jointly drive the rotation angle RX1 of the first mirror M-X1 and the rotation angle RX2 of the second mirror M-X2, in order to obtain the centering of the axis of the beam tilted on the axis of the microscope objective. The electronic system is adapted as a function of the configuration of the mirrors M-X1 and M-X2 and of the distances A and B.

As indicated in the table 2, a tilting angle θ of the axis 12 of the scanning laser beam limited to a few degrees is sufficient to angularly displace the beam over all of the optical field of the most common objectives. However, as indicated hereinabove, the rotation angle RX2 of the second mirror is equal to half of the tilting angle θ of the beam. And the rotation angle RX1 of the first mirror is equal in absolute value to double the rotation angle RX2 (application of the approximate formula (III) hereinabove). The rotation angles of the first and second mirrors are therefore limited to a few degrees in order to cover the entire optical field of the microscope objective while still remaining centered on the pupil of the microscope objective. However, a low rotation angle of the first mirror makes it possible to limit the displacement amplitude of the beam on the face of the second mirror and thus to limit the vignetting effect.

It is observed that the size of the mirrors M-X1 and M-X2 can be different. Preferably, the second mirror M-X2, has a larger size than the first mirror M-X1. Indeed, the first mirror M-X1 is centered on an incident laser beam that remains with a fixed direction while the second mirror M-X 2 offsets the displacement of the laser beam on its surface during the rotation of the first mirror M-X1.

The principle detailed in FIG. 6 for an axis of angular displacement (X) of the beam is generalized to a scanning system according to two axes (XY). For this for example, there is in series on the optical path of the beam, a first optical system with two mirrors mobiles in rotation, for example about an axis Y in order to produce a displacement according to a first direction X (as detailed in FIG. 6) and a second similar optical system with two mirrors mobiles in rotation, for example about an axis X in order to produce a displacement according to a transverse direction Y. The four mirrors are arranged in such a way that the angular displacement of the beam by the first two mirrors remains centered on the entrance pupil of the second optical system with two mirrors, and in such a way that an angular displacement according to one, the other or both transverse axes, remains centered on the center O of the entrance pupil of the microscope objective.

Preferably, the microscope is of the confocal type and the beam scanning system is arranged advantageously on the common laser-detection path, and more precisely between the injection-rejection filter 18 and the microscope objective 1.

Alternatively, in a less advantageous non-confocal microscope, the beam scanning system is arranged on the laser path only.

Figure 7:
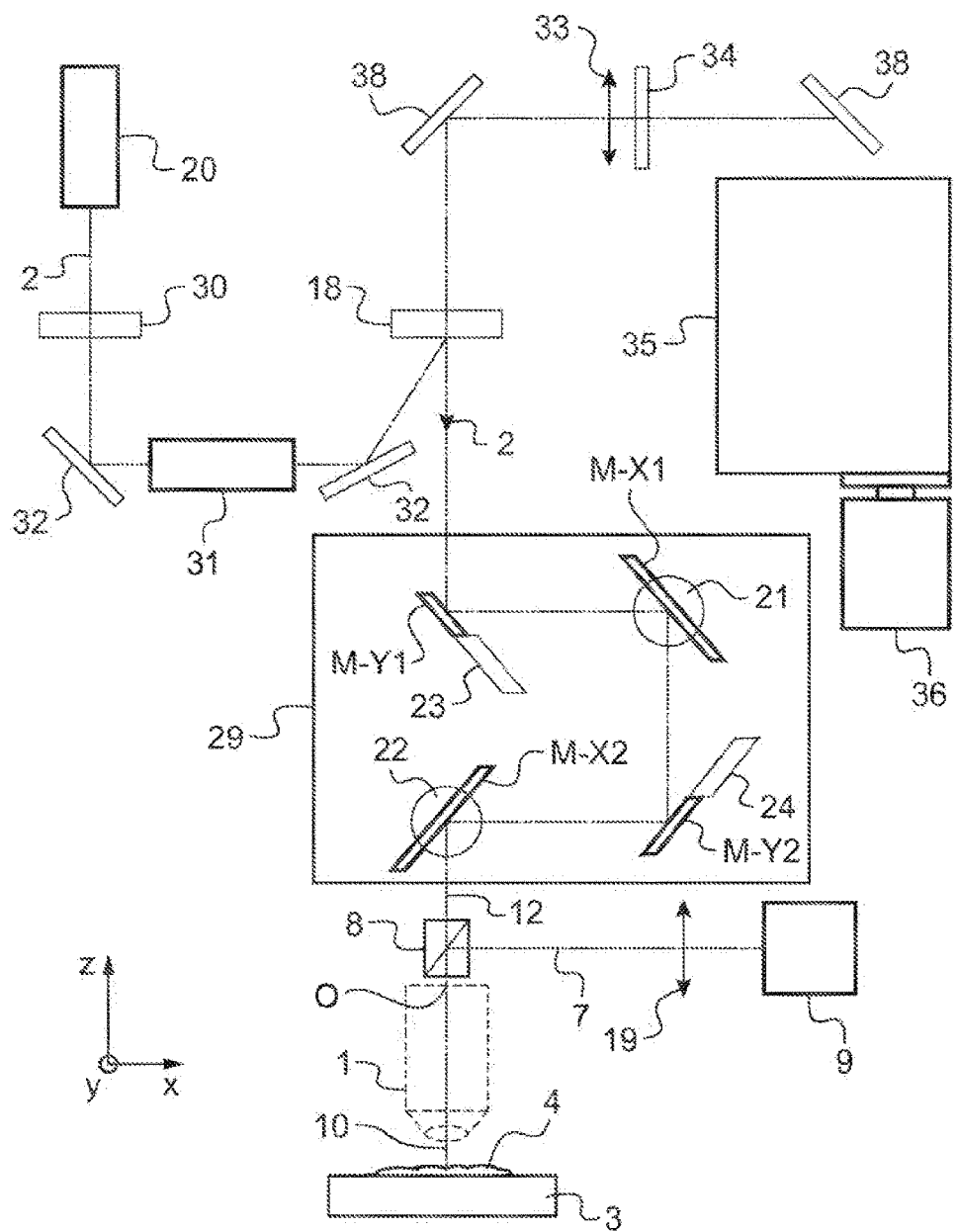
FIG. 7 diagrammatically shows an apparatus for Raman micro-spectrometry comprising a device with two scanning axes according to a second embodiment of the invention.

FIG. 7 shows as a side view a microscopy apparatus comprising a scanning laser beam device along two scanning axes according to a second embodiment of the invention. The laser beam scanning microscopy apparatus comprises a laser source 20, a filter wheel 30, an optical system with mirrors 32 on the path of the laser beam, a beam expander 31, an injection-rejection filter 18. The source laser 2 emits a laser beam 2, comprising one or several wavelengths. Advantageously, the filter wheel 30 makes it possible to select a particular wavelength for the excitation beam. The microscopy apparatus also comprises a microscope objective 1 having an entrance pupil with center O. A sample holder 3 supports a sample 4 arranged in the focal plane of the objective 1. Advantageously, the microscopy apparatus comprises a focusing lens 33 and a confocal hole 34 arranged in a plane that is optically conjugated with the focal plane of the microscope objective 1. The apparatus of FIG. 7 comprises a spectrometer 35, a detector 36 and another optical system with mirrors 38 on the path of the Raman scattering beam. Finally, the apparatus of FIG. 7 comprises an optical system 19 and a viewing camera 9. The apparatus of FIG. 7 applies in particular to Raman microspectrometry.

More particularly, the microscopy apparatus comprises an optical device 29 for the angular displacement or scanning of the laser beam. This optical device for the beam scanning 29 is placed between the injection-rejection filter 18 and the microscope objective 1.

The optical system for beam scanning 29 with two scanning axes (X, Y) comprises a flat mirror M-Y1, a flat mirror M-X1, a flat mirror M-Y2 and a flat mirror M-X2 disposed in series on the optical path of the laser beam 2. The mirrors M-X1, M-X2, M-Y1 and M-Y2 are actuated respectively by actuators 21, 22, 23 and 24. As described in detail hereinabove, the combined rotation movements of the mirrors M-X1 and M-X2 about an axis parallel to the Y axis make it possible to angular displace the axis of the laser beam by rotation about an axis parallel to the Y axis and passing through the center O of the pupil of the objective. Similarly, the combined rotation movements of the mirrors M-Y1 and M-Y2 about an axis parallel to the X axis make it possible to angular displace the axis of the laser beam by rotation about an axis parallel to the X axis and passing through the center O of the pupil of the microscope objective. Thus, the optical system with mirrors M-X1, M-X2, M-Y1, M-Y2 makes it possible to angularly displace the laser beam according to one or two transverse directions over a larger surface of the sample without vignetting of the laser beam while still remaining centered on the pupil of the microscope objective.

In FIG. 7, by way of example a beam expander 31 is used. A beam expander is an optical system that makes it possible to multiply the size of an optical beam. A beam expander is for example formed from an afocal optical system with a magnification greater than 1. Two beam expanders disposed in series on the optical path of the source beam, upstream of the optical scanning 29, can also be used.

Recall the following notions of optics:

1) the numerical aperture (NA) of an objective, for example of a microscope, depends on the diameter of its lens and on the distance to the focal point according to the following formula:

$$NA = n.\sin(\theta) = \frac{nD/2}{\sqrt{f^2 + D^2/4}} \quad (III)$$

2) when a laser enters into a microscope objective 1, it focuses in one point at the distance from the focal point. The size of this point can depend on three factors: the size of the laser beam, the diameter of the lens of the objective and its numerical aperture (NA).

In the case where the laser beam can cover all of the aperture of the lens, i.e. when the diameter of the beam is greater than or equal to the lens diameter, the size of the beam at the point focal depends solely on the diameter of the lens and on its numerical aperture (NA). In this case, the minimum diameter of the focal spot is defined by Airy's formula as being equal to:

$$(0.51*\lambda)/NA \quad (IV)$$

By application of formula (IV), in the case where the diameter of the laser beam is greater than or equal to the lens diameter, the larger the diameter of the lens is, the smaller the focal spot is.

In the case where the diameter of the laser beam is less than the lens diameter, the larger the diameter of the laser beam is, the smaller the focal spot is, with as a limit the formula (IV). The formula (IV) can also be applied by considering that the effective diameter of the lens is defined by the diameter of the laser beam.

The effect of a beam expander 31 is to enlarge the diameter of the laser beam on the entrance pupil of the objective. The size of the beam in the focal plane of the objective is determined by application of the diffraction limit. Therefore, the larger the diameter of the collimated laser beam is on the entrance pupil of the objective, the smaller the dimension of the beam in the focal plane is. Using a beam expander thus makes it possible to increase the spatial resolution of the microscopy apparatus and the signal-to-noise ratio of the Raman signal for a confocal microscope. Indeed, the smaller the Airy spot is, the more light can be coupled in a small confocal hole. In imaging applications with microscopic resolution, it is thus possible to carry out the imaging faster.

The magnification of the beam expander is selected in order to increase the diameter of the laser beam in such a way that the diameter at $1/e^2$ of the laser beam reaches the diameter of the pupil of the microscope objective used, which corresponds to a compromise between spatial resolution and signal-to-noise.

Advantageously, different types of beam expanders are used: a beam expander with fixed magnification and a beam expander with variable magnification. For example, two expanders being disposed in series on the path of the incident beam 2, the first beam expander has a fixed magnification equal to ×2 and the second beam expander with variable magnification has a variable magnification of ×1 to ×4.5.

For example, an objective 10× has a diameter of 9 mm, an objective 50× has a diameter of 5.4 mm and an objective 100× has a diameter of 3.24 mm.

A beam expander with variable magnification makes it possible to adjust the diameter of the laser beam according to the diameter of the pupil of the microscope objective used, in a microscopy apparatus that has several microscope objectives.

Advantageously, the beam expander with variable magnification is of the achromatic type in the visible range (400-700 nm). Preferably, the beam expander with variable magnification 31 is motorized. Advantageously, a self-aligning mirror, arranged on the optical path immediately after the beam expander, makes it possible to correct the pointing error of a beam expander with variable magnification.

The diameter of the laser beam emitted by the laser source can be measured, for example by means of a camera of the Gentec brand "Laser Beam Imager" and by means of its processing software. The transverse dimensions of the laser beam are measured using the so-called 4Sigma method, without the beam expander: 1183 μm according to the X axis and 1261 μm according to the Y axis.

A measurement is then taken via the same method of the diameter of the laser beam at the output of the beam expander with variable magnification, with the magnification being set to the maximum (X4,5) according to the data of the manufacturer. The transverse dimensions of the laser beam are measured at the output of the beam expander: 5494 μm according to the X axis and 5346 μm according to the Y axis. These measurements correspond to an average multiplication of 4.44 times, which is coherent with the value indicated by the manufacturer, which is 4.5.

The use of a beam expander is particularly easy in a microscopy apparatus of the confocal type, where the beam expander 31 can be inserted directly into the confocal tube of the microscope without any other optical adaptation, with the beam expander being arranged on the laser path only or on the common Raman laser-signal path.

The combination of a beam expander 31 and of a beam scanning system 29 by pivoting about the center of the pupil of the microscope objective makes it possible to benefit from conjugated advantages in order to increase the width of the zone of angular displacement of the beam on the sample while still increasing the spatial resolution of the laser beam at the focal point. This combination thus makes it possible to solve the two main limitations of the scanning laser beam system of prior art.

An apparatus for scanning laser beam microscopy according to any embodiment is advantageously used in an application for Raman microspectrometry. In this application, the system for angularly displacing the beam is disposed, on the optical path of the excitation laser beam, more preferably between an injection-rejection filter and the microscope objective. On the excitation beam the injection-rejection filter 18 directs the incident laser beam 2 to the scanning system with mirrors 29 in the direction of the microscope objective 1. The scanning system with mirrors 29, for example M-X1, M-Y1, M-X2, M-Y2, makes it possible to angularly displace the laser beam on the sample 4 according to one or two scanning axes. In a back-scattering configuration, the microscope objective 1 collects the back-scattered beam which comprises the Rayleigh scattering at the wavelength of the incident laser beam, and the Raman scattering beam, which is offset in wavelength. The beam collected by the microscope objective 1 is transmitted to the scanning system with mirrors 29 (M-X1, M-Y1, M-X2, M-Y2), then to the injection-rejection filter 18. By construction, the back-scattered beam follows the reverse optical path of the incident laser beam and therefore exits the scanning system with mirrors exactly in the direction of the incident laser beam, with this direction remaining fixed regardless of the tilting angle of the scanning beam on the microscope objective. Advantageously, the injection-rejection filter 18 spatially separates the Rayleigh scattering beam from the Raman scattering beam. An optical system with mirrors 38 then directs the Raman scattering beam to a Raman spectrometer 35 which spectrally separates the Raman scattering beam in the direction of a detector 36 in order to detect and to analyze the Raman back-scattering signal.

This Raman microspectrometry apparatus makes it possible to analyze a larger surface of the sample, while still improving the signal-to-noise ratio and the spatial resolution of the excitation laser beam on the sample.

In the apparatus of FIG. 7 which comprises an injection-rejection filter 18 (of the notch, edge, beam splitter, or epifluoresence filter type) and a confocal hole 34, the scanning mirrors are arranged on the confocal path which makes it possible to remain in the configuration of a confocal microscope. Another beam expander can be inserted on the confocal path in order to correctly cover the pupil of the objective.

The apparatus of FIG. 7 further comprises a camera 9, provided with a focusing lens 19. A beam splitter 8, for example a cube beam splitter, is arranged on the optical path of the laser beam between the optical system with mirrors 29 and the microscope objective 1. This beam splitter 8 makes it possible to direct a beam 7 formed by reflection and/or scattering on the sample 4 to the camera in such a way as to form an image of the surface of the sample and/or of the laser beam. Advantageously, the apparatus also comprises a white light source (not shown), with the white light beam being inserted on the optical axis of the microscope, for example between the beam splitter 8 and the microscope objective 1, in such a way as to illuminate the object field of the sample 4 with white light. This lighting with white light makes possible, by reflection and/or scattering, a better visualization of the sample 4 via the camera 9. In this way, the camera 9 makes it possible to simultaneously view the sample and the position of the laser beam during its angular displacement in the optical field of the camera. Advantageously, the magnification of the objective of the camera is selected in such a way as to allow for the visualization of the entire zone of angular displacement of the laser beam and/or of the entire optical field of the microscope objective. In an alternative, the objective of the camera is a variable focus objective.

Figure 8:
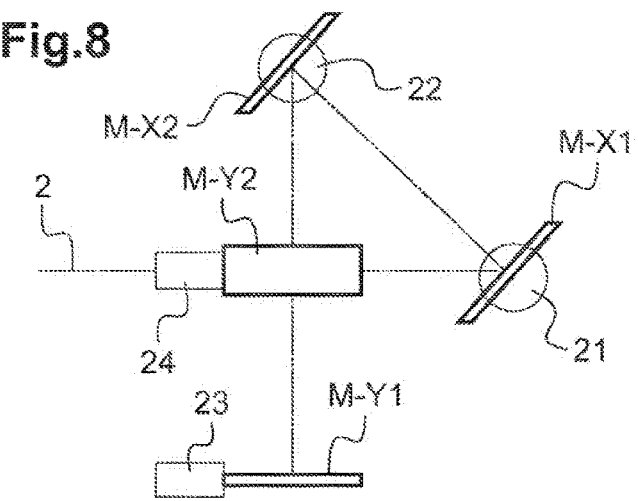
FIG. 8 shows an alternative configuration of the mirrors in the second embodiment of the invention.
Figure 9:
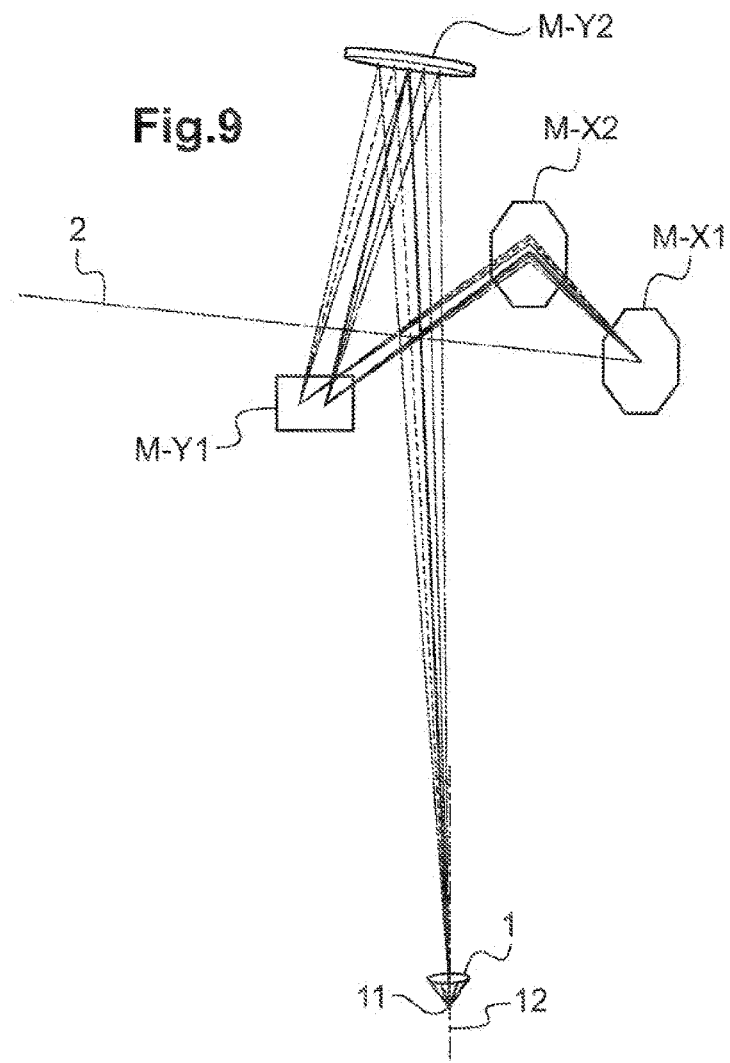
FIG. 9 shows a plot diagram of rays in a system with two scanning axes of the system with mirrors of FIG. 8.

FIG. 8 shows as a top view an optical beam scanning system with two axes according to a first alternative of the second embodiment of the invention. In this alternative, the incident laser beam 2 is directed and reflected successively by the first mirror M-X1, the second mirror M-X2, the third mirror M-Y1 then the fourth mirror M-Y2, with the axis of the beam reflected by the fourth mirror M-Y2 being perpendicular to the plane of FIG. 8. FIG. 9 shows, via a ray tracing diagram, the optical system with two scanning axes of FIG. 8. This arrangement of mirrors makes it possible, using a horizontal laser beam source, to form a scanning laser beam that has an axis 12 dose to the axis 10 of the microscope objective 1, with this optical axis 10 being generally vertical. The advantage of this alternative is to be very compact and to avoid having to add an additional flat reflector mirror.

Figure 10:
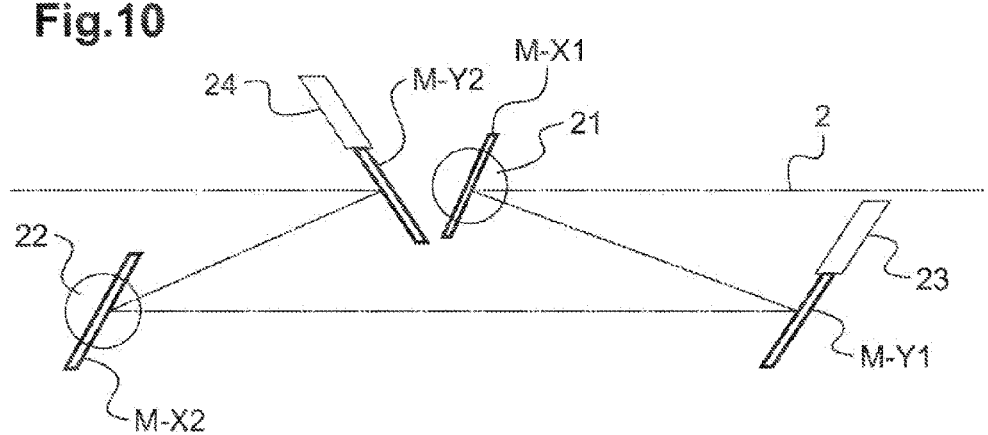
FIGS. 10-15 show various alternative configurations of the mirrors in a system with two laser beam scanning axes according to the second embodiment of the invention.
Figure 11:
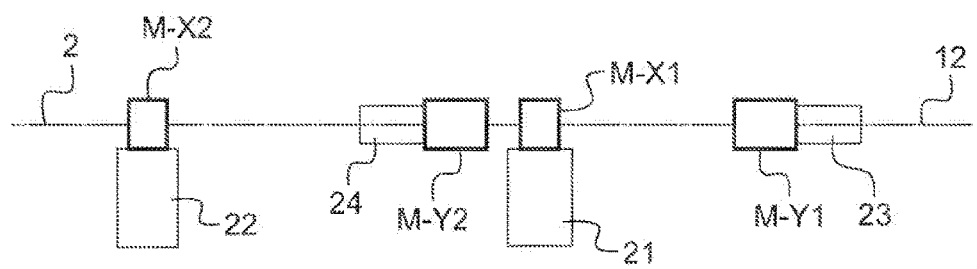

FIGS. 10 and 11 show respectively as a top view and as a side view a second alternative of the configuration of the mirrors in a system with two scanning axes of a laser beam according to the second embodiment of the invention. In this alternative, the incident laser beam 2 is successively reflected by the flat mirror M-X1, the flat mirror M-Y1, the flat mirror M-X2 and the flat mirror M-Y2. The angle of incidence of the laser beam 2 on the first mirror M-X1 is chosen in such a way as to be less than about 45 degrees and more preferably less than 22.5 degrees relatively to the normal to the surface of the mirror M-X1. Advantageously, the angles of incidence on the other mirrors M-Y1, M-X2 and M-Y2 are also chosen to be as low as possible, in such a way as to increase the apparent surface of the mirrors. In addition, limiting the angle of incidence makes it possible to reduce the apparent diameter or the spreading of the laser beam on each one of the mirrors M-X1, M-Y1, M-X2 and M-Y2. This alternative thus makes it possible to use an incident laser beam 2 with a wider diameter, which makes it possible in particular to improve the spatial resolution of the scanning microscope. This alternative with a dosed angle also makes it possible to reduce the effect of anamorphosis due to the tilting of the mirror. Indeed, a 45 degrees tilted mirror scanning symmetrically angularly according to the two axes produces a rectangular figure with a ratio as a square root of 2 between the two axes. This can be applied in particular to mirrors with two axes with an actuator of the voice coil type.

Figure 12:
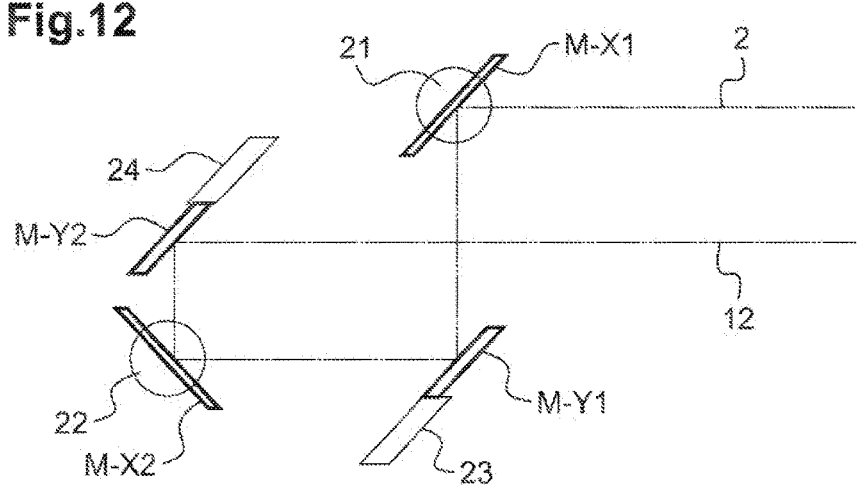
Figure 13:
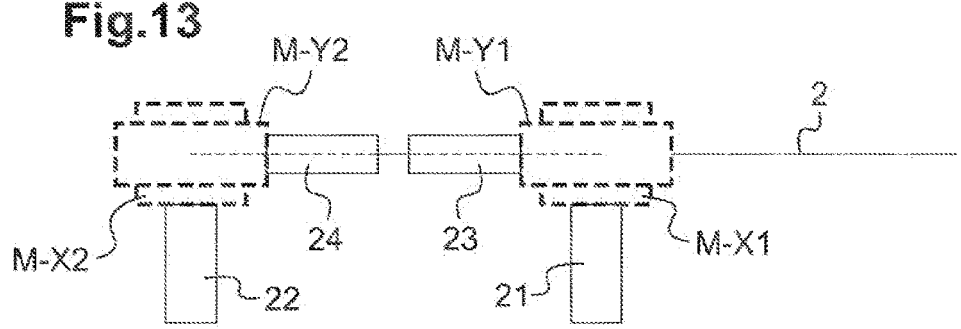

FIGS. 12 and 13 show respectively as a top view and as a side view a third alternative of the configuration of the mirrors in a system with two scanning axes of a laser beam according to the second embodiment of the invention. In this alternative, the incident laser beam 2 is successively reflected by the flat mirror M-X1, the flat mirror M-Y1, the flat mirror M-X2 and the flat mirror M-Y2, the axis 12 of the scanning beam being located in a direction that is globally parallel to the direction of the incident beam 2. This alternative makes it possible to fold back the laser scanning beam and thus reduce the encumbrance of the beam scanning optical system.

Figure 14:
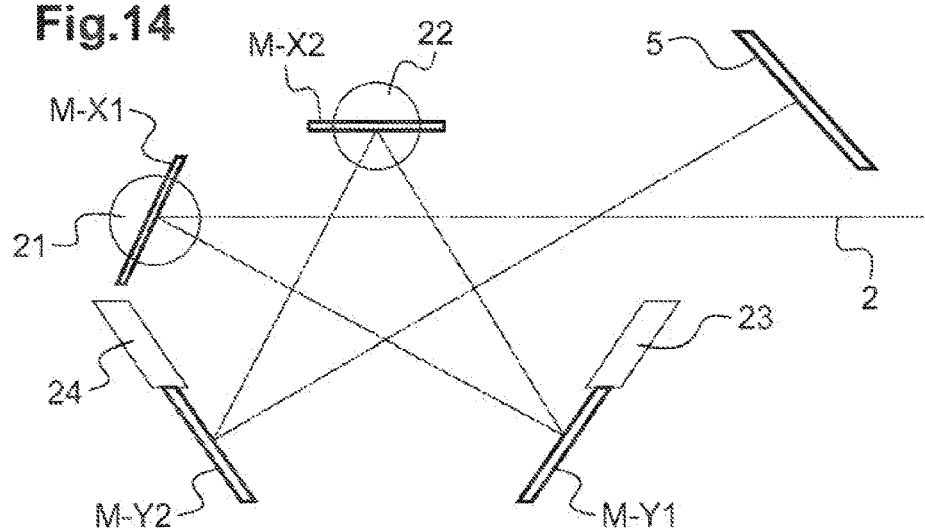
Figure 15:
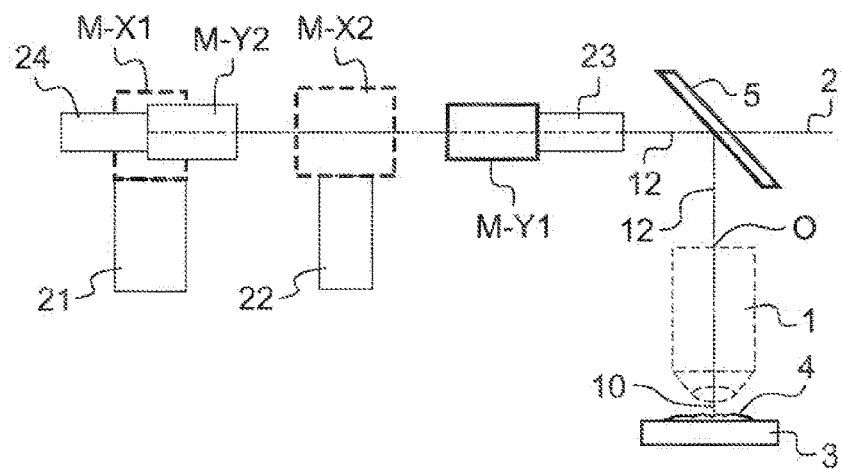

FIGS. 14 and 15 respectively show as a top view and as a side view a fourth alternative of the configuration of the mirrors in a system with two scanning laser beam axes according to the second embodiment of the invention. In this alternative, the incident laser beam 2 is successively reflected by the flat mirror M-X1, the flat mirror M-Y1, the flat mirror M-X2, the flat mirror M-Y2 and a flat reflector mirror 5 in order to direct the beam to the microscope objective 1. This alternative allows for both a savings in space by folding back the scanning laser beam and a reduction in the angle of incidence of the beam on the mirrors which makes it possible to reduce the spreading and/or to increase the diameter of the laser beam.

FIGS. 16 to 18 show a laser beam scanning system according to two scanning axes according to a third embodiment of the invention. FIG. 16 is a top view, the FIG. 17 a side view of a first alternative of the third embodiment. FIG. 18 shows a perspective view of a second alternative of the third embodiment.

In this embodiment, a first flat mirror M-XY1 is used and a second flat mirror M-XY2. The first mirror M-XY1 is mounted on an actuator 25 with two axes of rotation, for example of the piezoelectric type or a voice coil (Moving coil or Voice Coil). Thus, the first actuator 25 makes it possible to carry out a rotation about an axis X and/or about an axis Y. Preferably, the axis of rotation of the first actuator 25 about the X axis and the axis of rotation of this first actuator 25 about the Y axis cross at a point located in the vicinity of the surface of the first mirror M-XY1. Likewise, the second flat mirror M-XY2 is mounted on an actuator 26 with two axes of rotation, for example of the piezoelectric type or a voice coil, with the actuator 26 making it possible to carry out a rotation about an axis X and/or about an axis Y. Preferably, the axis of rotation of the second actuator 26 about the X axis and the axis of rotation of this second actuator 26 about the Y axis cross at another point located in the vicinity of the surface of the second mirror M-XY2. The movements of rotation about each axis are combined between the first actuator and the second actuator in such a way that the beam reflected on the two mirrors M-XY1 and M-XY2 pivots around a point aligned on the center O of the pupil of the microscope objective. This configuration makes it possible to reduce the number of mirrors to only two mirrors, instead of four as in the embodiments described hereinabove. The reduction in the number of mirrors makes it possible to bring more laser light on the sample and to collect more Raman scattered light, therefore to obtain an image faster. In addition, this third embodiment makes it possible to use mirrors of larger dimension, which allows for an angular displacement of the laser beam of greater amplitude and better spatial resolution in X, in Y and/or in Z. Finally, this third embodiment makes it possible to use mirrors that are thicker, for example dielectric mirrors, which have better efficiency.

By comparison, in a prior beam scanning system, called duoscan, wherein the mirrors are of small dimension, and are mounted in a removable manner in order to make it possible to collect more Raman flow and to not vignette the field of the viewing camera. On the contrary, with the system of the invention, the mirrors do not limit the collection of the Raman signal or the field of the image of the viewing camera, and do not need to be mounted on removable supports. The mounting is thus simplified.

In the first alternative shown in FIGS. 16-17, the axis of the incident laser beam 2 is globally parallel to the axis 12 of the scanning laser beam at the output of the optical system with mirrors.

In the second alternative shown in FIG. 18, the axis of the incident laser beam 2 is globally transverse to the axis 12 of the scanning laser beam at the output of the optical system with mirrors.

An advantage of this third embodiment is to reduce the number of mirrors used to two instead of four in the preceding embodiments, which reduces the losses of intensity on the laser scanning beam and on the signal collected. From this, stems the possibility of using mirrors M-XY1 and M-XY2 that are larger than the mirrors M-X1, M-X2, M-Y1 and M-Y2 used in the embodiments described in relation with FIGS. 8-15.

Another advantage of this third embodiment is to have an extremely reduced encumbrance.

Particularly advantageously, the mirrors M-X1, M-Y1, M-X2, M-Y2, M-XY1 and M-XY2 are of the dielectric type, with the dielectric processing being adapted to increase the effectiveness in reflection. Preferably, the dielectric mirrors have a wide spectral bandwidth (for example 325 nm-1100 nm, or 325-1700, or 325-2200 nm), which makes it possible to use the same mirrors for the entire spectrum from ultraviolet (UV) to near infrared (NIR).

The system and the method for scanning a laser beam can be combined with different components in order to provide additional advantages.

However, at a high scanning speed (of about 30 Hz for an actuator or scanner of the voice coil type), the various scanners can be subjected to uncontrolled phase shifts, the recentering on the center O of the pupil of the objective no longer works and the laser scanning is then irregular, and vignetted. A means for correcting this defect while still operating at a higher scanning speed (i.e. up to a few hundred Hz) is to set up a phase locked loop by using the signals from position sensors of the first mirror (for example M-X1 or M-XY1) generally provided with each scanner, in order to control the phase of the control signal of the second mirror (M-X2 or M-XY2), and this for each scanning axis.

Particularly advantageously, the Raman scattering signal is integrated over several measuring points during the angular displacement of the beam, in such a way as to record an averaged Raman signal over several points, as described in patent document WO2008128971A2. The use of the scanning of one or two axes according to an embodiment of this invention makes it possible to extend the scanning zone on the sample and/or to increase the spatial resolution of the Raman microspectrometry measurements and/or to increase the signal-to-noise ratio of the Raman microspectrometry measurements.

In the case where a beam expander is used in a scanning laser beam Raman microspectrometry apparatus, the beam expander is arranged on the path of the excitation laser beam, but outside of the optical path of the Raman scattering beam. Advantageously, the beam expander is arranged between the laser source and a splitting filter, for example of the injection-rejection filter or notch filter type.

The scanning beam system is compatible with different microscope objectives. In particular, it is possible to use a microscope objective with a mirror, for example an objective of the Cassegrain or Schwartzfield type. An objective with a mirror has the advantage of being achromatic, which allows for spectrometry measurements with better precision. It is thus easier to separate an excitation laser beam and a Raman scattering beam. On the other hand, in microscopy, the achromatism of the microscope objective provides an axial detection at the same point as the excitation laser, which is important in particular in the case of a transparent sample.

The scanning with two axes makes it possible to better couple the laser light with an objective of the Cassegrain type because it is possible to illuminate the edge of the primary mirror and not the center. Indeed, the laser rays passing through the center of the primary mirror are retro-reflected and do not reach the sample to be analyzed, leading to substantial losses. This invention therefore advantageously makes it possible to convey more laser light to the sample by using an objective of the Cassegrain or Schwartz-field type.

The scanning device of the invention can also be combined advantageously with a system of conic lenses, such as described for example in patent document WO/2013/014379A, in order to form a conic or cylindrical laser beam. Preferably, the aperture of the conic or cylindrical beam is sufficient to cover the pupil of the objective and thus make it possible to increase the intensity of the output beam. This device can also replace a system of conic lenses, such as described in document FR1156687 in order to form using a rapid scanning a hollow cylindrical laser beam with any section (for example annular or other) which does not have or which has very little light on the axis of the cylinder. This has the advantage in particular of suppressing the central rays and of illuminating the sample only with tilted rays outside of the axis. This type of lighting makes it possible to substantially reduce the contribution of the substrate to the confocal Raman signal. This type of lighting also makes it possible to substantially reduce the optical aberration referred to as longitudinal spherical aberration, which appears during the refraction in an index environment and which induces a degradation of the spatial resolution of a confocal microscope.

FIGS. 19-22 show various measurements of the scanning width obtained with a laser scanning microscopy apparatus according to the embodiment described in relation with FIG. 7.

In place of the sample 4 is arranged a calibration pattern certified by UKAS (United Kingdom Accreditation Service) in accordance with the requirements of the NIST (National Institute of Standards and Technology). This test patter comprises a scale 20 mm long with graduations spaced every 0.01 mm. The pattern makes it possible to measure the maximum displacement of the beam in the focal plane of the microscope objective during a scanning according to an axis parallel to the axis of the pattern.

In order to measure the zone of displacement in a scanning microscopy apparatus according to two axes, a successive measurement is taken of the maximum displacement by orienting the pattern according to the X axis then according to the Y axis.

Figure 19:
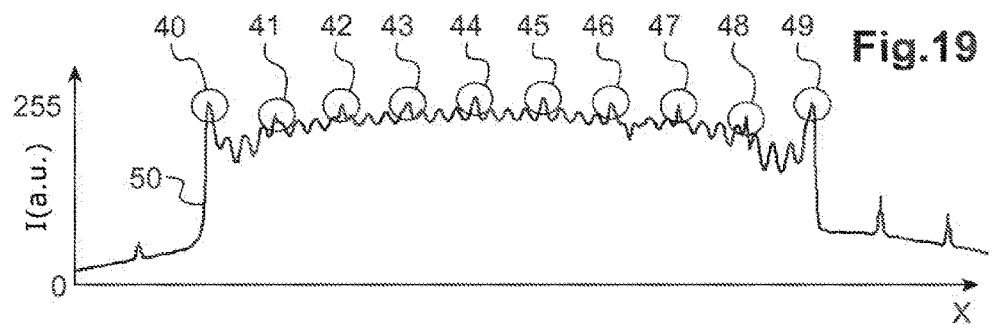
FIGS. 19-22 show various measurements obtained with an apparatus for laser scanning microscopy according to the invention.

FIG. 19 shows a measurement of the pattern to scale on a scanning beam microscopy apparatus provided with a microscope objective 10× during a scanning according to an axis parallel to the X axis, with the pattern oriented parallel to the X axis. More precisely, the curve 50 represents the measurement of the intensity of the signal reflected at the wavelength of the laser according to an angular displacement of the beam along the X axis over the pattern. The local maxima encircled 40, 41, . . . 49 in FIG. 19 correspond to a reflection of the laser on a bar of the scale of the pattern. It is observed that the maxima 40, 41, . . . 49 are spaced by 50 µm. The scanning width of the beam over the pattern according to the X axis corresponds to the distance between the first maximum 40 and the last maximum 49, i.e. about 450 microns. In addition, the average level of the curve 50 is representative of the homogeneity of the optical system. The higher and constant the average level is, the better the measurement is.

Figure 20:
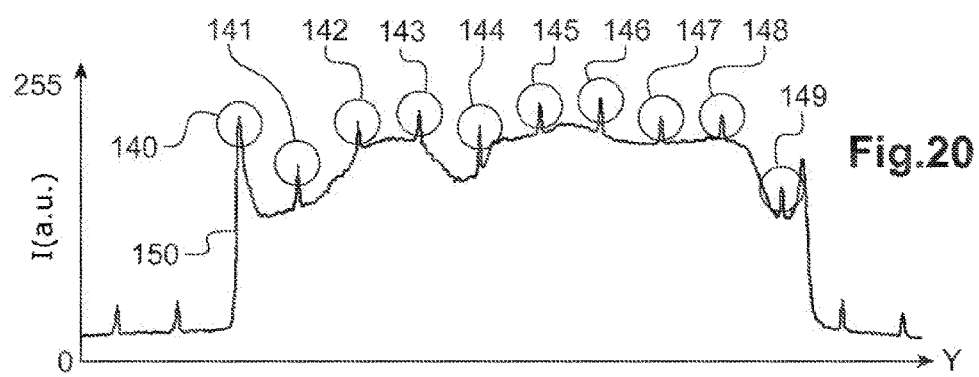

FIG. 20 shows a measurement of the same pattern on the same microscopy apparatus with the same microscope objective 10× during a scanning according to an axis parallel to the Y axis with the patter being oriented parallel to the Y axis. The curve 150 represents the measurement of the intensity of the signal reflected at the wavelength of the laser according to an angular displacement of the beam along the Y axis over the patter. The local maxima encircled 140, 141, . . . 149 in FIG. 20 correspond to a reflection of the laser on a bare of the scale of the pattern. It is checked that the maxima 140, 141, . . . 149 are spaced by 50 µm. The scanning width of the beam on the pattern according to the Y axis corresponds to the distance between the first maximum 140 and the last maximum 149, i.e. about 450 microns.

Screen captures on a viewing camera make it possible to confirm that the scanning width according to the X axis is about 460 µm and the scanning width according to the Y axis of about 470 µm.

By comparison with a scanning width of about 200 microns obtained with a Duoscan apparatus of prior art provided with an objective 10×, the scanning system of the invention therefore makes it possible to increase the field width by a factor of about 2.2 times higher in each direction X, Y, and therefore to increase the scanned surface by a factor of about 4.9.

Figure 21:
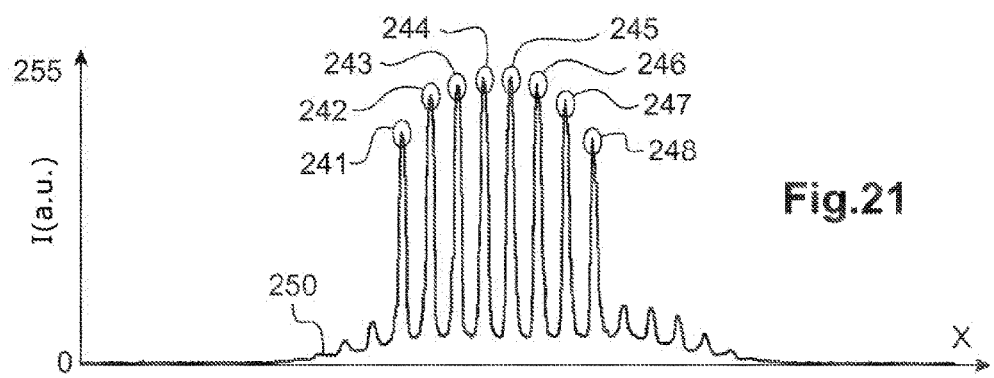

FIG. 21 shows a measurement of the same patter to scale on a scanning beam microscopy apparatus provided with a microscope objective 50× during a scanning according to an axis parallel to the X axis, with the pattern being oriented parallel to the X axis. The local maxima encircled 240, 241, . . . 248 on the curve 250 of FIG. 21 correspond to a reflection of the laser over a bar of the scale of the pattern. It is observed that the maxima 241, . . . 248 are spaced about 10 µm. The scanning width of the beam on the pattern according to the X axis corresponds to the distance between the first maximum 241 and the last maximum 248, i.e. about 70 microns.

Figure 22:
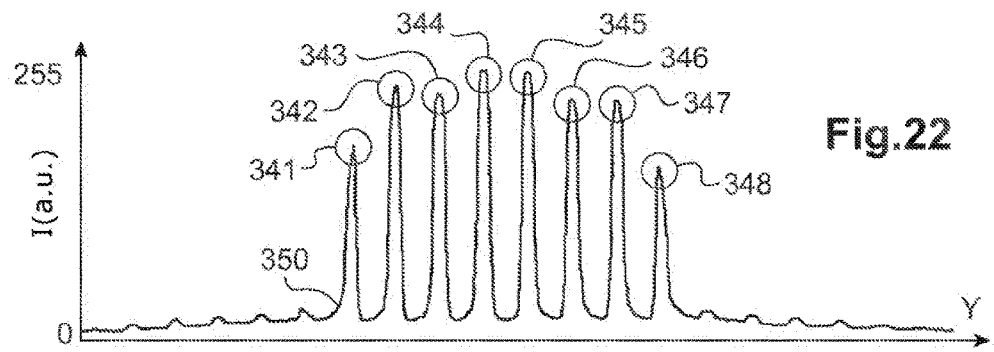

FIG. 22 shows a measurement of the same pattern on the same microscopy apparatus with the same microscope objective 50× during a scanning according to an axis parallel to the Y axis with the pattern being oriented parallel to the Y axis. The local maxima encircled 341, 342 . . . 348 on the curve 350 of FIG. 22 correspond to a reflection of the laser over a bar of the scale of the pattern. It is observed that the maxima 341, 342 . . . 348 are spaced about 10 µm. The scanning width of the beam on the patter according to the Y axis corresponds to the distance between the first maximum 341 and the last maximum 348, i.e. about 70 microns.

Screen captures on a viewing camera make it possible to confirm that the scanning width with the objective 50× according to the X axis is about 70 µm and the scanning width according to the Y axis of about 70 µm.

By comparison with a scanning width obtained with a Duoscan apparatus of prior art provided with an objective 50×, the scanning system of the invention therefore makes it possible to increase the field width by a factor of about 2.7 times higher in each direction X, Y, and therefore to increase the scanned surface by a factor of about 7.6.

Alternatively, instead of using a test pattern with a one dimension scale, a flat test patter in two dimensions comprised of squares of 0.5*0.5 mm comprised themselves of squares of 0.01*0.01 mm is used. This square pattern is used to form an image of the surface scanned by reflection. The image makes it possible to view the squares of the pattern and to observe the scanning of the laser beam on the pattern. Advantageously, the square pattern is illuminated with white light in order to allow for an image regardless of the position of the laser beam.

With an objective 10×, it is estimated that the extent of the displacement of the beam is about 440 µm*450 µm. A darkening of the image on the edges of the scanning is due to the vignetting on the edges of the mirrors mounted on the scanners, with the intensity of the beam decreasing when the beam reaches the edge of a mirror or the edge of the pupil of the objective.

For an objective 50×, it is observed with the square pattern, that the scanning zone that can be used is about 80*75 µm.

The invention claimed is:

1. An apparatus for optical beam scanning microscopy comprising:
    at least one light source configured to emit an optical beam;
    a microscope objective having an entrance pupil, the microscope objective being arranged according to a longitudinal optical axis of the microscopy apparatus, the pupil having a center on the longitudinal optical axis and the microscope objective being configured to focus said optical beam in an object plane transverse to the longitudinal optical axis; and
    an angular displacement system configured to angularly displace the optical beam according to two transverse spatial directions in the object plane, the angular displacement system consisting of:
        a first mirror and a second mirror disposed in series on the optical path of the optical beam between the light source and the microscope objective,
        the first mirror being mounted on an actuator with two axes of rotation configured to tilt said first mirror according to a first predetermined rotation angle around a first rotation axis and configured to tilt the first mirror according to a third predetermined rotation angle around a second rotation axis transverse to the first rotation axis,
        the second mirror being mounted on another actuator with two axes of rotation configured to tilt said second mirror according to a second predetermined rotation angle as a function of said first rotation angle, around the first rotation axis and configured to tilt the second mirror according to a fourth predetermined rotation angle as a function of the third rotation angle around the second rotation axis transverse to the first rotation axis, to angularly tilt the axis of the optical beam by pivoting about the center of the pupil of the microscope objective, said optical beam remaining centered on the center of the pupil of the microscope objective in a range of tilting angles of the axis of the optical beam with respect to the longitudinal optical axis, to displace the optical beam according to said two directions in the object plane.

2. The apparatus for optical scanning microscopy according to claim 1, wherein the actuator of the first mirror is a piezoelectric or voice coil actuator, and/or wherein the other actuator of the second mirror is a piezoelectric or voice coil actuator.

3. The apparatus for optical beam scanning microscopy according to claim 1, wherein the actuator of the first mirror comprises a position sensor that supplies a position signal, and
    wherein the other actuator of the second mirror comprises a position sensor,
    the apparatus further comprising a phase locked loop system configured to drive a control signal of the other actuator of the second mirror as a function of the position signal of the actuator of the first mirror.

4. The apparatus for optical beam scanning microscopy according to claim 1, wherein the second rotation angle is a function of the first rotation angle, the distance B between the first mirror and the second mirror, and the distance A between the second mirror and the center of the entrance pupil of the microscope objective.

5. The apparatus for optical beam scanning microscopy according to claim 1, wherein said at least one light source comprises one or several sources of the laser source and/or light-emitting diode type.

6. The apparatus for optical beam scanning microscopy according to claim 1, further comprising a beam expander disposed between the light source and the microscope objective, the beam expander having a fixed and/or variable magnification.

7. The apparatus for optical beam scanning microscopy according to claim 1, further comprising a viewing camera configured to form an image of the object plane of the microscope objective and/or to view a zone of a sample scanned with optical beam scanning.

8. The apparatus for optical beam scanning microscopy laser according to claim 1, further comprising a confocal hole disposed in a plane optically conjugated with the object plane and comprising an optical system configured to collimate the optical beam disposed between the at least one light source and the microscope objective in order to form a collimated optical beam, the first mirror and the second mirror being disposed in series on the optical path of the collimated optical beam.

9. The apparatus for optical beam scanning microscopy according to claim 1, wherein the microscopy apparatus is combined with a Raman spectrometer, a coherent anti-Stokes Raman spectrometer, a fluorescence spectrometer, a photoluminescence spectrometer, or a cathodoluminescence spectrometer configured to measure and analyze a signal by reflection, transmission and/or scattering of the optical beam on the sample as a function of an angular displacement of the optical beam.

10. A method for optical beam scanning microscopy comprising:
    emitting an optical beam by a light source;
    optically reflecting said laser beam on a first mirror then on a second mirror disposed in series on the optical path of the laser beam between the light source and a microscope objective;
    tilting said first mirror according to a first predetermined rotation angle around a first rotation axis and tilting the first mirror according to a third predetermined rotation angle around a second rotation axis transverse to the first rotation axis;
    tilting said second mirror according to a second predetermined rotation angle as a function of the first rotation angle around the first rotation axis and tilting the second mirror according to a fourth predetermined rotation angle as a function of the third rotation angle around the second rotation axis transverse to the first rotation axis, to angularly tilt the axis of the optical beam by pivoting about the center of the pupil of the microscope objective, in a range of tilting angles of the axis of the optical beam with respect to a longitudinal optical axis; and focusing said optical beam in an object plane by via said microscope objective, to displace said optical beam according to at least one spatial direction in the object plane.

* * * * *